United States Patent [19]

Voth et al.

[11] Patent Number: Plant 5,262

[45] Date of Patent: Jul. 24, 1984

[54] STRAWBERRY PLANT 'CHANDLER'

[75] Inventors: Victor Voth, Santa Ana; Royce S. Bringhurst, Davis, both of Calif.

[73] Assignee: The Regents of the University of California, Berkeley, Calif.

[21] Appl. No.: 452,699

[22] Filed: Dec. 23, 1982

[51] Int. Cl.[3] ..... A01H 5/03

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new and distinct variety of strawberry plant of the short-day type primarily charcterized as an early fruiter in both winter and summer plantings in south and central coastal California. Runner production in nursery plantings is considered excellent and exceeds 'Tioga'. Flowers are self fertile with little malformed fruit which otherwise is long conic to long flat wedgy and usually solid. The variety has flavor comparable to the best flavored varieties used in California and fruit is much firmer than 'Douglas' making the variety suitable for fresh and processing markets.

3 Drawing Figures

DESCRIPTION

This invention relates to a new and distinctive short-day type strawberry cultivar designated as 'Chandler' which is the result of a cross of 'Douglas' (U.S. Plant Pat. No. 4,487) × Cal 72.361-105 = C55 (U.S. Plant Pat. No. 4,481) made in 1977.

'Chandler' first fruited at the University of California Wolfskill Experimental Orchards near Davis in 1979 where it was selected and designated originally as Cal 77.32-103. It was tested later as advanced selection C24.

'Chandler' has been propagated asexually by runners and has been tested at various University of California field stations and facilities and to a very limited extent in a few growers' fields under Test Agreement.

Figure 1:
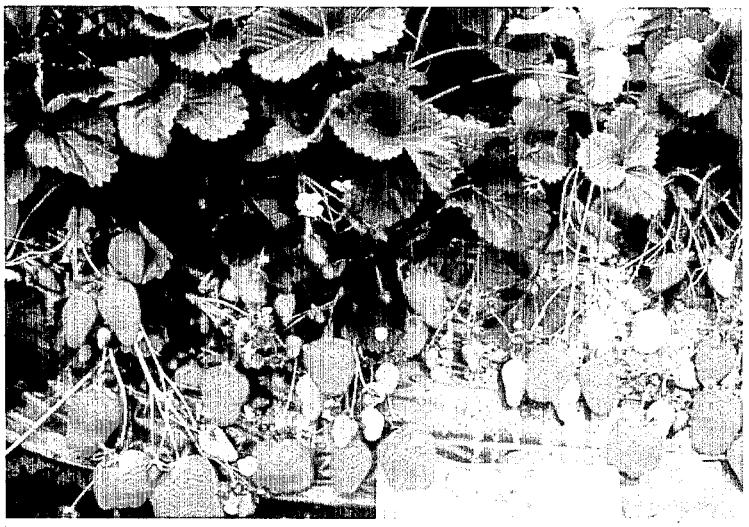
FIG. 1 shows typical growth, flowering and fruiting characteristics of the plant.
Figure 2:
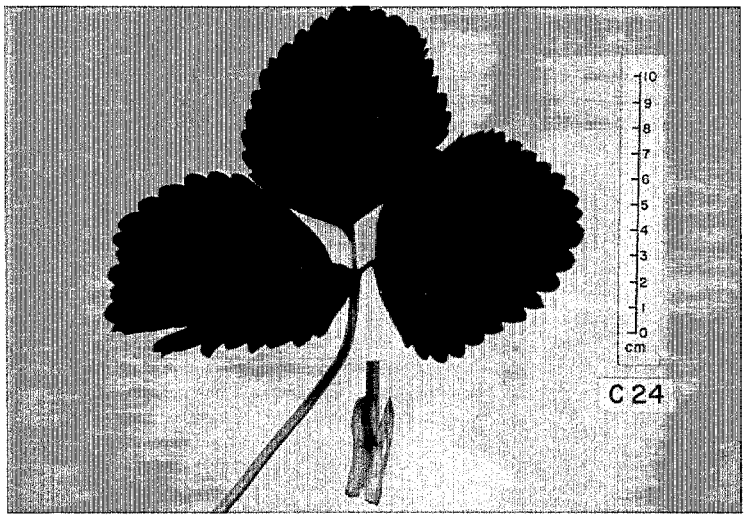
FIG. 2 shows a typical midsummer mature leaf from a plant in full fruit.
Figure 3:
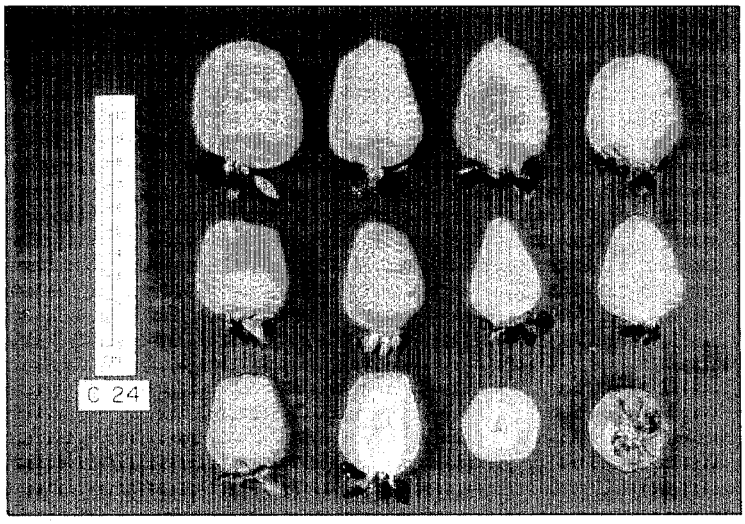
FIG. 3 shows representative early-season fruit with longitudinal and cross-sectional views.

'Chandler' is early fruiting and has performed well in winter and summer planting experiments in south and central coastal California. It is just a little later than 'Douglas' and the fruit is much firmer.

PLANTS AND FOLIAGE

'Chandler' plants are semi-erect in growth habit, about the same size as those of the standard 'Tioga' in both winter and summer plantings as estimated by measuring petiole length on plants in full fruit. Leaflets of 'Chandler' are about the same size as those of 'Tioga' averaging about one serration more per terminal half leaf. Leaves are about the same color and intensity as those of 'Tioga', 2.5GY4/3 (Munsell Color System-Nickerson Color Fan). Runner production in nursery plantings is excellent, better than 'Tioga'.

ISOZYMES IN LEAF EXTRACTS

'Chandler' has been classified for three enzyme systems: (A) Phosphoglucoisomerase (PGI); (B) Leucine Amino Peptidase (LAP); and (C) Phosphoglucomutase (PGM); identical to 'Aliso' but different from 'Tioga', 'Tufts', 'Douglas', 'Aiko' and 'Pajaro':

| | 'Tioga' | 'Tufts' | 'Douglas' | 'Aiko' | 'Pajaro' | 'Chandler' & 'Aliso' |
|---|---|---|---|---|---|---|
| PGI | A1 | A2 | A3 | A4 | A4 | A1 |
| LAP | B1 | B3 | B3 | B3 | B3 | B3 |
| PGM | C3 | C4 | C1 | C2 | C1 | C1 |

*1981 J. Amer. Soc. Hort. Sci. 106: 684–687

FLOWERING AND FRUITING

'Chandler' flowers are borne on medium long, semi-erect peduncles which are brought down quickly by the weight of the fruit. The flowers are self fertile with ample pollen throughout the season and consequently there is little malformed fruit.

FRUIT APPEARANCE

'Chandler' fruit is long conic to long flat wedgy. Internally the fruit is usually solid throughout to slightly hollow. The fruit skin color is about 5R4/12 (ibid), about the same color as that of fully colored 'Pajaro'. The finish is glossy and attractive. The flesh is about the same as the skin throughout. The achenes are bright yellow positioned flush with surface to slightly embedded. The calyx is medium to small in size borne on a distinct neck and reflexed. The fruit is about as firm and durable as that of 'Tioga', 'Tufts' or 'Aiko' according to penetrometer readings and handling comparisons. The fruit size averages larger than that of 'Tioga' with a wide range in size as the season advances.

FRUIT QUALITY

'Chandler' has averaged higher ascorbic acid content (34 mg/100 g fress fruit) than 'Tioga' (23), 'Tufts' (27) or 'Douglas' (28), but lower than 'Pajaro' (36) and 'Aiko' (41), as tested on summer and winter plantings during 1981 and 1982 by the method of Loeffler and Ponting (1942, J. Indust. and Engin. Chem 14:846). Soluble solids readings were not significantly different from those of 'Tioga', 'Tufts', 'Douglas', 'Aiko' or 'Pajaro' from comparable plantings. The flavor of 'Chandler' is excellent comparable to that of the best flavored cultivars now used in California in our opinion and according to most who have tried it. It is suitable for fresh market and processing.

We claim:

1. The new and distinct variety of strawberry plant herein described and illustrated and identified by the characteristics enumerated above.

* * * * *